US011141513B2

(12) United States Patent
Locke et al.

(10) Patent No.: US 11,141,513 B2
(45) Date of Patent: Oct. 12, 2021

(54) FLUID CONTAINER WITH PRESSURE REGULATION

(71) Applicant: KCI Licensing, Inc., San Antonio, TX (US)

(72) Inventors: Christopher Brian Locke, Bournemouth (GB); Benjamin Andrew Pratt, Poole (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 404 days.

(21) Appl. No.: 16/073,226

(22) PCT Filed: Jan. 25, 2017

(86) PCT No.: PCT/US2017/014832
§ 371 (c)(1),
(2) Date: Jul. 26, 2018

(87) PCT Pub. No.: WO2017/132199
PCT Pub. Date: Aug. 3, 2017

(65) Prior Publication Data
US 2019/0030221 A1 Jan. 31, 2019

Related U.S. Application Data

(60) Provisional application No. 62/288,142, filed on Jan. 28, 2016.

(51) Int. Cl.
*A61M 1/00* (2006.01)

(52) U.S. Cl.
CPC ........ *A61M 1/0011* (2013.01); *A61M 1/0001* (2013.01); *A61M 1/743* (2021.05);
(Continued)

(58) Field of Classification Search
CPC .............. A61M 1/0001; A61M 1/0011; A61M 1/0035; A61M 5/14586; A61M 16/08;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Chinese First Office Action for Corresponding Application No. 2017800068504, dated Aug. 26, 2020.
(Continued)

*Primary Examiner* — Tatyana Zalukaeva
*Assistant Examiner* — Meagan Ngo (57) ABSTRACT

A system or apparatus may include a container configured to collect fluid from a tissue site and regulate negative-pressure from a negative-pressure source. In some embodiments, the container may include a regulator that receives negative pressure directly from an unregulated negative-pressure source, such as a wall-suction outlet. The regulator may regulate down the pressure delivered to a collection chamber in the container, which may in turn be connected to a tissue site.

29 Claims, 7 Drawing Sheets (52) U.S. Cl.
CPC .............. *A61M 1/82* (2021.05); *A61M 1/90* (2021.05); *A61M 2205/16* (2013.01); *A61M 2205/3331* (2013.01)

(58) Field of Classification Search
CPC .... A61M 27/00; A61M 5/145; A61M 1/0072; A61M 2205/3331; F04B 43/00; G12B 1/04
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,167,621 A * | 12/1992 | Band ................. | A61M 1/0023 604/35 |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,542,939 A * | 8/1996 | Onodera .............. | A61M 1/0009 417/469 |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,174,306 B1 * | 1/2001 | Fleischmann ........ | A61B 17/085 604/540 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0292263 A1 * | 11/2009 | Hudspeth .............. | A61M 27/00 604/313 |
| 2013/0144227 A1 * | 6/2013 | Locke ................. | A61M 1/0035 604/318 |
| 2014/0163491 A1 | 6/2014 | Schuessler et al. | |
| 2014/0188061 A1 * | 7/2014 | Locke ................. | A61M 1/0009 604/321 |
| 2015/0018784 A1 * | 1/2015 | Coulthard ........... | A61M 1/0031 604/319 |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |

(56) References Cited

FOREIGN PATENT DOCUMENTS

| | | | |
|---|---|---|---|
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 2010245 A1 * | 1/2009 | .......... A61M 1/0088 |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 9611031 A1 | 4/1996 | |
| WO | 97/18007 A1 | 5/1997 | |
| WO | 99/13793 A1 | 3/1999 | |
| WO | 2004110523 A1 | 12/2004 | |
| WO | 2009062915 A1 | 5/2009 | |
| WO | 2013/078214 A1 | 5/2013 | |
| WO | 2015006041 A1 | 1/2015 | |

OTHER PUBLICATIONS

International Search Report and Written Opinion for corresponding Application No. PCT/US2017/014832, dated Mar. 30, 2017.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its (56) References Cited

OTHER PUBLICATIONS

Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

FLUID CONTAINER WITH PRESSURE REGULATION

CROSS-REFERENCE TO RELATED APPLICATIONS

This application is the National Stage of International Application No. PCT/US2017/014832, entitled "Fluid Container With Pressure Regulation," filed Jan. 25, 2017 and claims the benefit of U.S. Provisional Patent Application No. 62/288,142, entitled "Fluid Container With Pressure Regulation," filed Jan. 28, 2016, all of which are incorporated herein by reference for all purposes.

TECHNICAL FIELD

The invention set forth in the appended claims relates generally to tissue treatment systems and more particularly, but without limitation, to fluid containers with pressure regulation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for regulating pressure in a negative-pressure therapy environment are set forth in the appended claims. Illustrative embodiments are also provided to enable a person skilled in the art to make and use the claimed subject matter.

Various embodiments of a system or apparatus for negative-pressure treatment are described. The system or apparatus may include a container configured to collect a fluid from a tissue site and regulate negative-pressure from a negative-pressure source. In some embodiments, for example, the container may include a regulator that receives negative pressure directly from an unregulated negative-pressure source, such as a wall-suction outlet. The regulator may regulate down the pressure delivered to a collection chamber in the container, which may in turn be connected to a tissue site.

In some embodiments, a container may include a lid or other apparatus for enclosing a canister. In general, the apparatus may comprise a rim configured to sealingly engage the fluid canister to form a collection chamber. The apparatus may further include a regulator adapted to regulate negative pressure in the collection chamber. In some embodiments, the regulator may generally comprise a regulator chamber, a first passage fluidly coupled to the regulator chamber, a second passage fluidly coupled to the regulator chamber, and a regulator valve. A downstream connector may be fluidly coupled to the first passage, and an upstream connector may be fluidly coupled to the second passage. In operation, the downstream connector may be fluidly coupled to a negative-pressure source, for example, and the upstream connector may be fluidly coupled to a dressing or other distribution component. The regulator valve may be configured to regulate fluid flow through the first passage based on changes to negative pressure in the regulator chamber. For example, if the downstream connector is coupled to a source of unregulated negative pressure, such as a wall-suction port, the regulator can regulate the negative pressure as it passes through the container to the dressing. In some embodiments, the regulator valve may be configured to close the first passage if negative pressure in the regulator chamber is greater than a target negative pressure, and to open the first passage if negative pressure in the regulator chamber is less than the target negative pressure.

In various embodiments, a negative-pressure treatment system is also described. The system may have a container having a collection volume configured to collect fluid from a tissue site. The system may further have a regulator having a regulator chamber that is integrated into the container configured to regulate negative pressure in the container from a reduced pressure provided by a primary negative-pressure source. A first passage from the regulator chamber may form a first fluid pathway between the regulator chamber and the tissue site and a second passage from the regulator chamber may form a second fluid pathway to the container.

The system or apparatus may further have an auxiliary or secondary negative-pressure source within the container, such as a collapsible internal reservoir within a canister lid. The reservoir may be inflated by one or more springs, if not under negative pressure. The springs may be designed or selected to collapse under a threshold negative pressure. The reservoir may be fluidly coupled to a regulator chamber through the second passage. In some embodiments, the reservoir may comprise or be defined by a flexible membrane, and a spring may be configured to bias the flexible membrane away from the regulator chamber. The reservoir may provide continued delivery of therapy if the container is removed from a primary negative-pressure source, such as a facility wall-suction port. A charge indicator may be incorporated into some embodiments of the container to indicate the state of the reservoir. In some embodiments, pressure regulation may be mechanical, and pressure feedback or indicators may be electronic.

In various embodiments, a method of forming a reduced pressure treatment system through a container to a tissue site to remove fluid from the tissue site into a collection volume of the container is disclosed. The method may comprise connecting a dressing at the tissue site to an upstream flow connection of the container and connecting a primary negative-pressure source to a downstream flow connection of the container. A regulator may be integrated into the container between the upstream flow connection and the downstream flow connection to regulate a first reduced pressure in the waste volume of the container from a second reduced pressure formed by the primary negative-pressure source.

Disclosed is a regulator system for a low pressure line or vacuum system. The regulator may be incorporated into a disposable unit, such as a container system. The regulator may regulate a vacuum source to a selected pressure.

The regulator may be incorporated into a container system that may be interconnected between an unregulated vacuum source and a tissue site. In particular, the regulator may be placed between an unregulated vacuum source and a dressing. The dressing may cover a portion of a wound, such as an ulcer, surgical incision site, or the like.

The regulator may be included in a canister or in a lid of a container system to assist in ensuring removal of the regulator to maintain proper operation of the regulator through appropriate duty cycles to maintain a regulated pressure. For example, a disposable regulator may ensure that the regulator does not become clogged during use and reduce or eliminate the regulated pressure. Therefore, the regulator may be incorporated into a container to allow the container to be disposed once full to allow replacement with a new container system having a new regulator that is clean.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. As should be recognized by those skilled in the art, however, this frame of reference is merely a descriptive expedient rather than a strict prescription.

Figure 1:
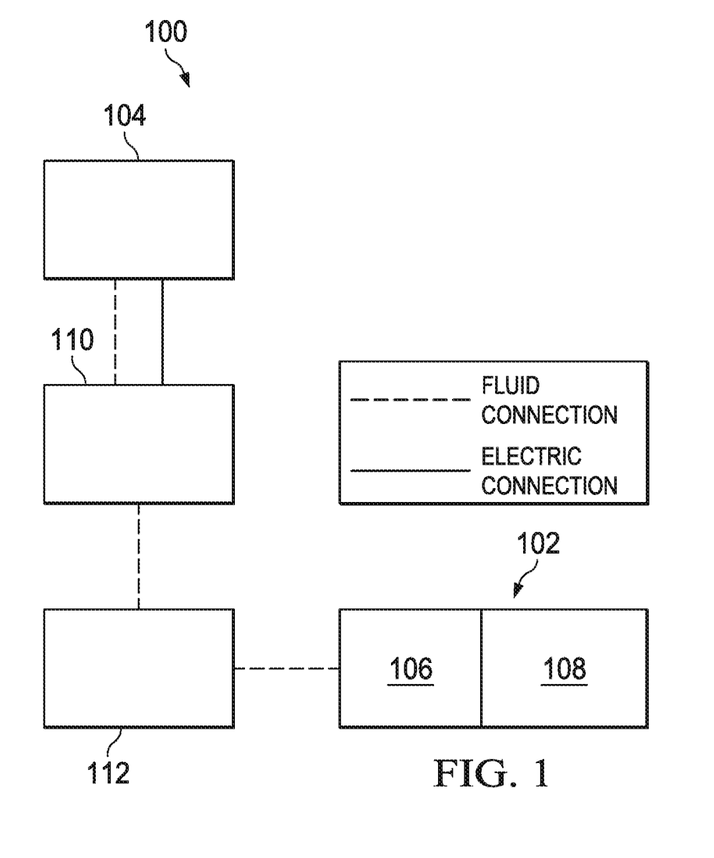
FIG. 1 is a functional block diagram of an example embodiment of a therapy system that can remove waste in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. Distribution components may include dressings, containers, and fluid conductors, for example. In FIG. 1, a dressing 102 is illustrative of a distribution component, which may be fluidly coupled to a negative-pressure source 104. A dressing may include a cover, a tissue interface, or both in some embodiments. The dressing 102, for example, may include a cover 106 and a tissue interface 108.

A regulator or a controller, such as a regulator 110, may also be coupled to the negative-pressure source 104. As illustrated in the example of FIG. 1, the regulator 110 may be fluidly coupled to the negative-pressure source 104 and to a fluid container, such as a container 112. In some embodiments, the therapy system 100 may optionally include sensors to measure operating parameters and provide feedback signals indicative of the operating parameters. For example, the negative-pressure source 104 may be electrically coupled to the regulator 110 to provide feedback signals or indicators.

In some embodiments, a dressing interface may facilitate coupling the negative-pressure source 104 to the dressing 102. For example, such a dressing interface may be a T.R.A.C.® Pad or Sensa T.R.A.C.® Pad available from KCI of San Antonio, Tex. The therapy system 100 may also include a fluid container, such as the container 112, coupled to the dressing 102 and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the regulator 110, and may be indirectly coupled to the dressing 102 through the regulator 110.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

Figure 2A:
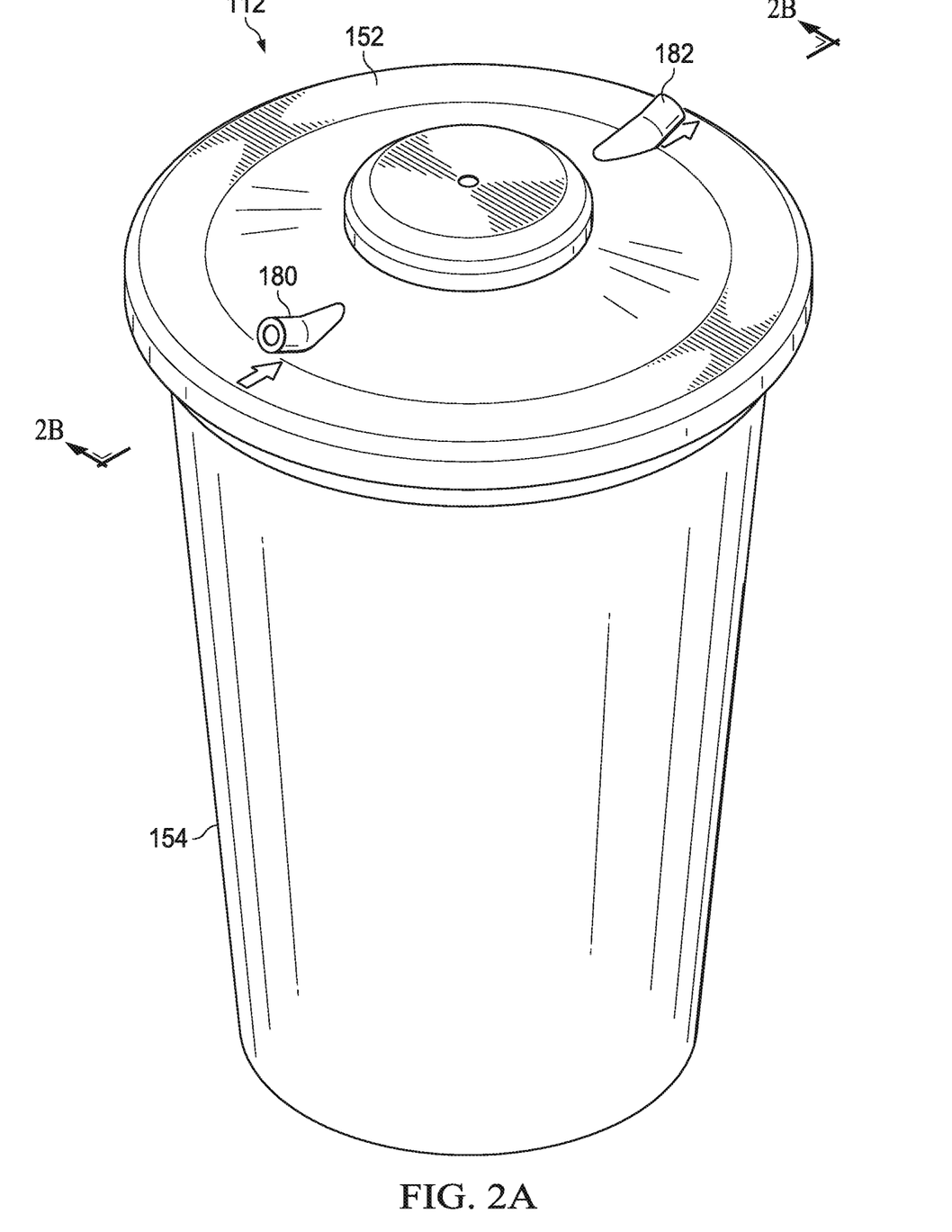
FIG. 2A is a schematic diagram illustrating additional details of the container system that may be associated with an example embodiment of therapy system of FIG. 1, according to various embodiments.
Figure 2B:
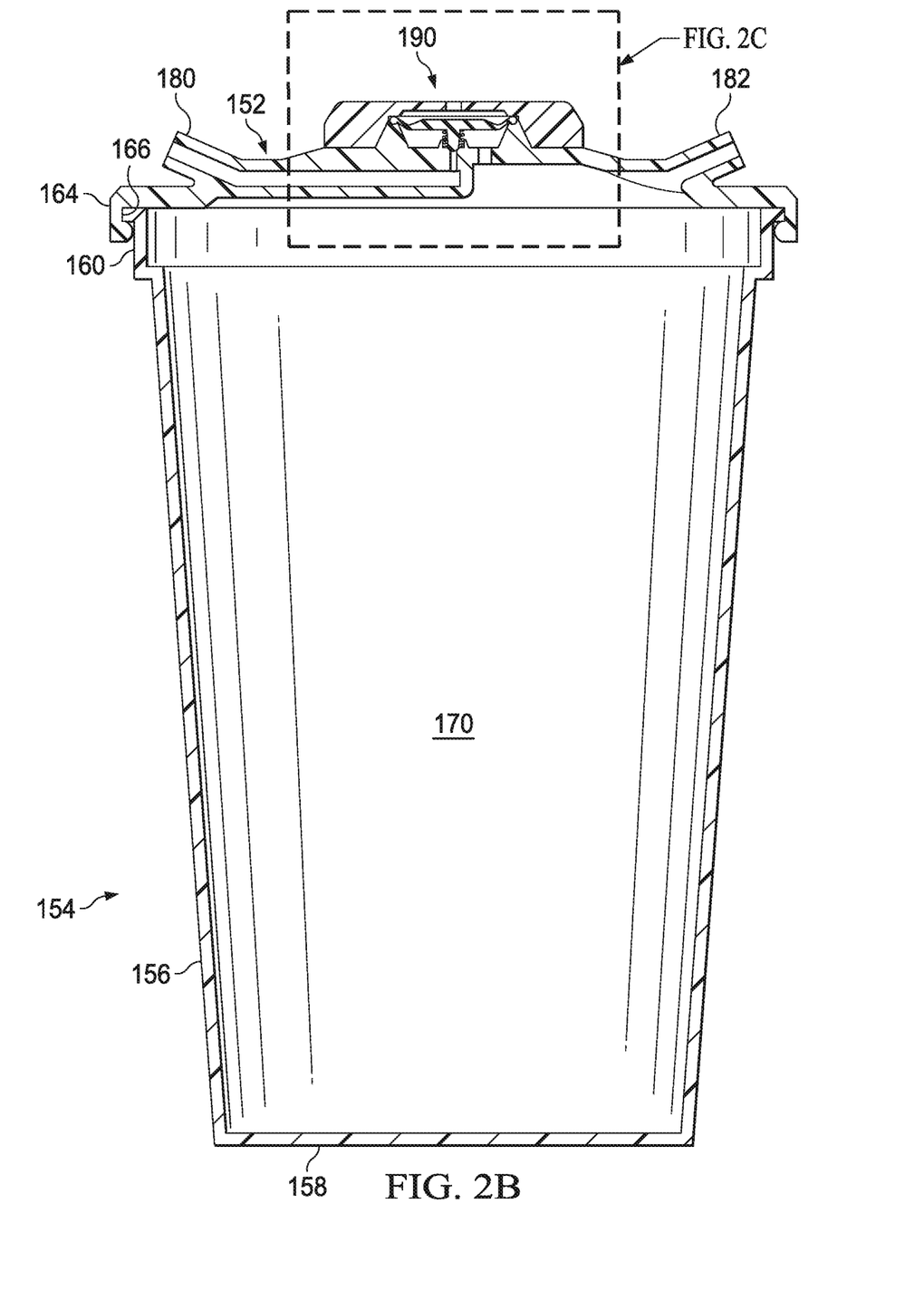
FIG. 2B is a cross-sectional view of the container of FIG. 2A along line 2B-2B.
Figure 2C:
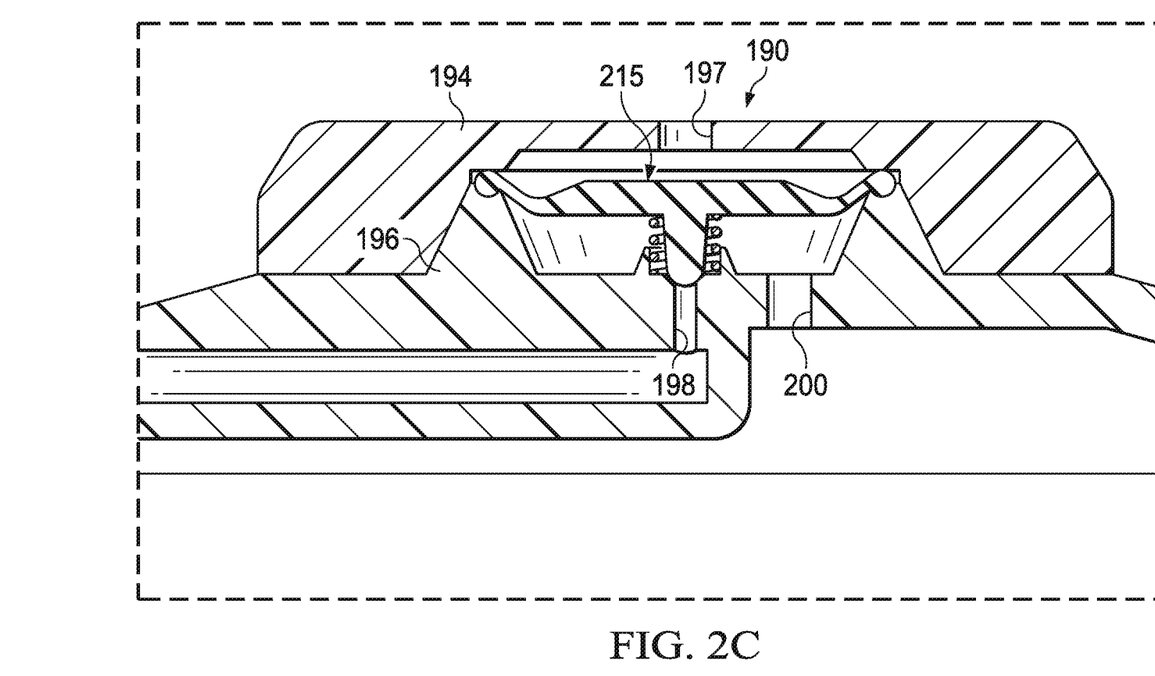
FIG. 2C is a detail of the container taken from Rectangle 2C of FIG. 2B.

FIGS. 2A-2C illustrate additional details that may be associated with some embodiments of the container 112. With reference to FIG. 2A, some embodiments of the container 112 may comprise a canister lid 152 and a canister 154. The canister 154 may be formed of various materials, including metals and/or polymers. Further, the canister 154 may be opaque, transparent, or semi-transparent. For example, the canister 154 may be any of a variety of suction canisters commonly found in health care facilities, such as suction canisters offered by BEMIS Health Care Products. Assembled as illustrated in the example of FIG. 2A, the canister lid 152 may be connected to the canister 154 with an air tight seal.

With continuing reference to FIG. 2A and additional reference to FIG. 2B, the canister 154 can include an external wall 156 that extends from a base wall 158 to an upper edge or rim, such as the rim 160. The rim 160 can sealingly engage the canister lid 152. For example, the canister lid 152 can include a lid connection portion or ledge 164 and the canister 154 can include a canister connection portion or ledge 166. The ledge 164 and the ledge 166 may form a snap fit, threaded connection, adhesive connection, or other appropriate connections. Generally, the canister lid 152 may be coupled to the canister 154 to form a collection chamber 170. The collection chamber 170 is preferably sealed relative to ambient environment. Further, the seal, such as formed by the ledge 164 and the ledge 166 is preferably an air-tight seal such that a negative pressure within the collection chamber 170 may be maintained for a selected period of time.

The canister lid 152 may include a first fluid port, such as a downstream connector 180. For example, the downstream connector 180 may be adapted for coupling with a tube or other fluid conductor, which can provide a fluid path between the negative-pressure source 104 and the container 112 as illustrated in FIG. 1. The canister lid 152 may further include a second fluid port, such as an upstream connector 182. For example, the upstream connector 182 may be fluidly coupled to the dressing 102, as illustrated in FIG. 1.

In various embodiments, the negative-pressure source 104 may provide substantially unregulated negative pressure, such as commonly available through wall ports in many health care facilities. The canister lid 152 may include various features to regulate pressure within the collection chamber 170. For example, in some embodiments, the canister lid 152 may include a regulator 190, which may be an example embodiment of the regulator 110 of FIG. 1. In various embodiments, the regulator 190 may be integrated into the lid 152, or may be connected to the lid 152. The regulator 190 may regulate the pressure from the negative-pressure source 104 to provide a pressure within a target range, such as a prescribed therapy range.

The regulator 190 can include various portions and generally may include an upper wall or cap 194, and a lower wall or base 196. The cap 194 may also have a vent 197. The regulator 190 may also generally comprise a fluid pathway between the downstream connector 180 and the upstream connector 182. In some embodiments, the fluid pathway may comprise a series of fluidly coupled passages. For example, as illustrated in the embodiment of FIG. 2C, the base 196 may include a first passage 198 fluidly coupled to the downstream connector 180, and a second passage 200, which may be fluidly coupled to the collection chamber 170.

The regulator 190 can include various portions to regulate distribution of negative pressure through the container 112. If the negative-pressure source 104 is unregulated, for example, the pressure within the collection chamber 170 may be regulated by the regulator 190.

The regulated pressure from the regulator 190 can be a regulated pressure that is a within a therapeutically acceptable range of pressure, for example, and may be substantially independent of the pressure provided by the negative-pressure source 104. Therefore, the regulator 190 can be interconnected between the negative-pressure source 104 and the dressing 102 to provide a target pressure to the dressing 102. Further, the regulator 190 can be substantially interconnected or included with the container 112 to provide regulated pressure through the tubing to the dressing 102 from an unregulated pressure source, such as the negative-pressure source 104.

Figure 3:
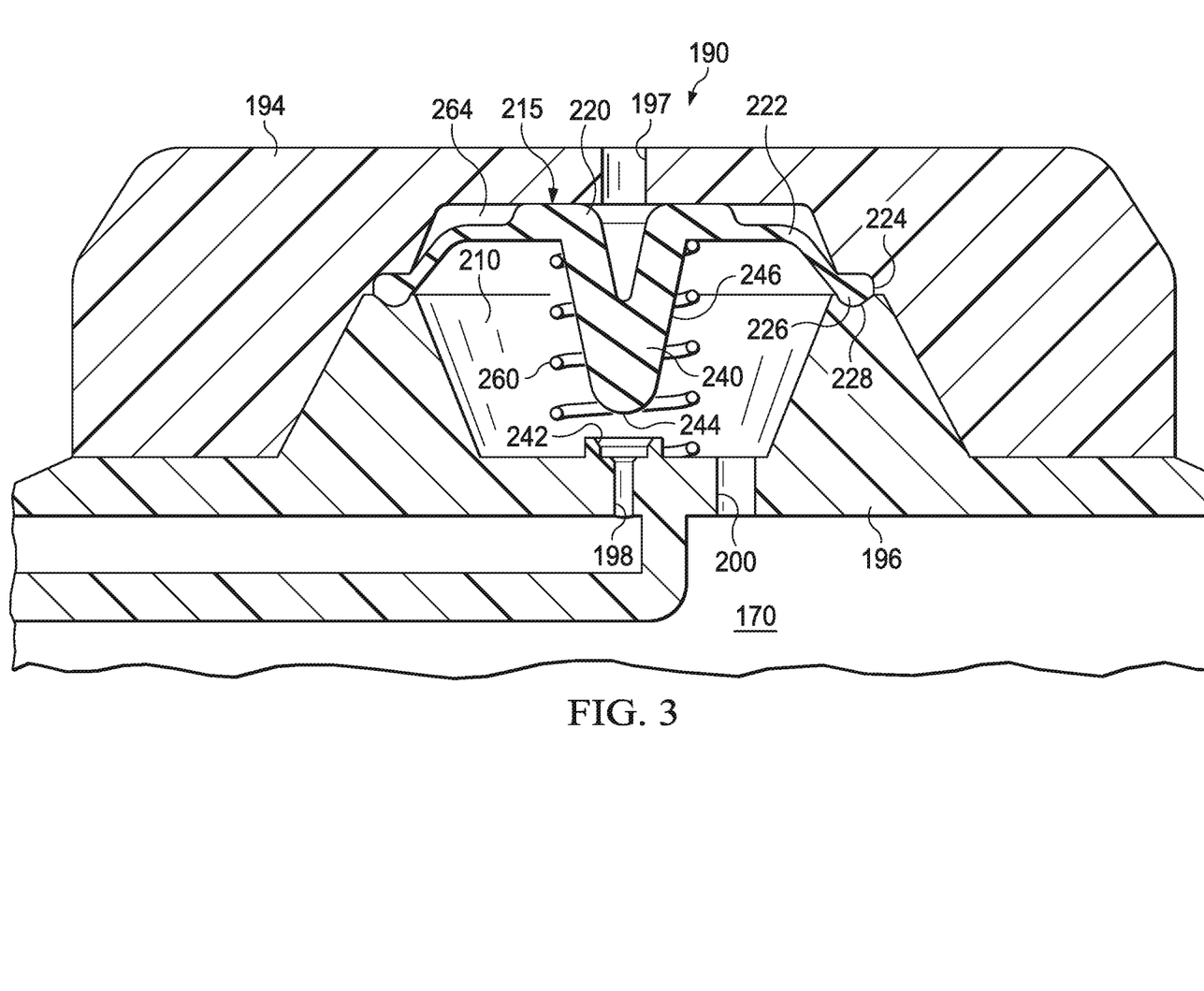
FIG. 3 is a detail cross-sectional view of a regulator in an open position.

FIG. 3 is a schematic diagram illustrating additional details that may be associated with some embodiments of the regulator 190. As illustrated in FIG. 3, the regulator 190 may include a regulator chamber 210 and a regulator valve 215 disposed between the cap 194 and the base 196. For example, as shown in the illustrative embodiment of FIG. 3, the regulator valve 215 may be a diaphragm valve having a regulator seal 220 and a regulator spring 260. The regulator seal 220 may be a flexible membrane or partition, such as a thin flexible disk. The regulator seal 220 may engage the base 196 at an outer edge 224. For example, the regulator seal 220 can be generally annular or circular, and configured to engage a similarly shaped portion of the base 196. In some embodiments, a projection or a protrusion 226 may engage an annular depression or groove 228 formed into the base 196. The cap 194 can assist in holding the protrusion 226 into the groove 228 to assist in operation of the seal 220.

In some embodiments, the regulator seal 220 may comprise a central portion 222, and a valve body 240 may extend from the central portion 222. The valve body 240 may be adapted to engage a valve seat 242 adjacent to the first passage 198 to seal the first passage 198. For example, an exterior wall or surface 246 of the valve body 240 can engage one or more surfaces of the valve seat 242 to close the first passage 198. As illustrated in FIG. 3, the valve body 240 may include an apex 244 to sealingly engage the valve seat 242.

The valve body 240 may be formed integrally and as one piece with the central portion 222. Alternatively, the valve body 240 may be formed as a separate piece from the central portion 222 and may be connected to the central portion 222. In various embodiments, the seal 220 and the valve body 240 may be formed of a flexible or an elastomeric material, which may include without limitation medical grade silicone.

The regulator spring 260 may be operatively engaged with the regulator seal 220 to bias the valve body 240 away from the first passage 198, providing an open fluid path between the first passage 198 and the second passage 200. For example, one end of the regulator spring 260 may be positioned concentrically around the valve seat 242 while the other end of the regulator spring 260 may be positioned around the valve body 240. The spring may be formed of various materials such as medical grade stainless steel, or other appropriate materials.

For example, the regulator spring 260 may provide a biasing force against ambient pressure provided through the vent 197, urging the valve body toward an open position (as illustrated in FIG. 3) and allowing fluid communication through the first passage 198. In the open position, the central portion 222 may be moved into a depression, hollow area, or recess, such as a recess 264 formed by the cap 194.

Figure 4:
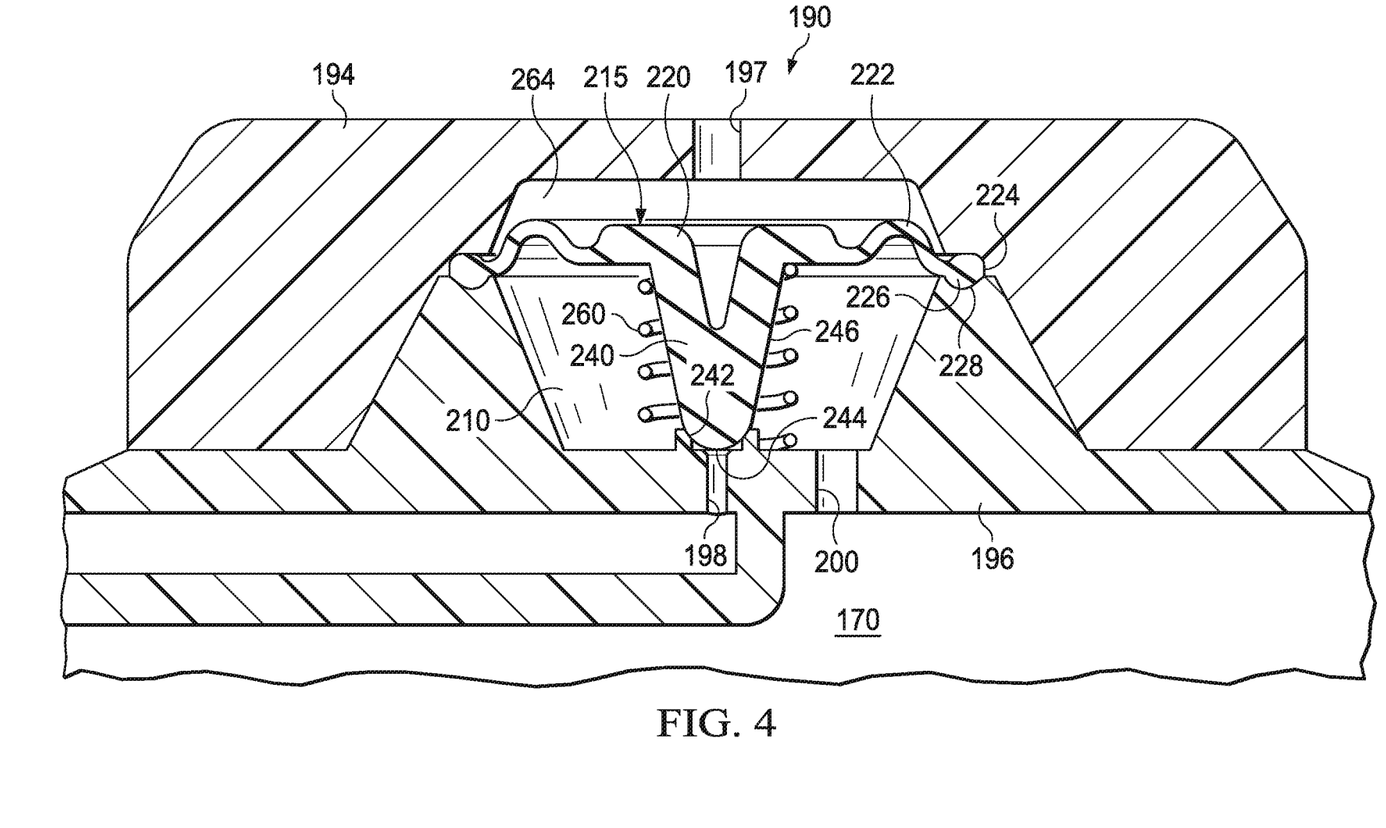
FIG. 4 is a detail cross-sectional view of a regulator in a closed position.

FIG. 4 illustrates additional details that may be associated with some embodiments of the regulator 190 in a closed position. In a closed position, the valve body 240 is at least moved partially out of the recess 264 of the cap 194 to close the first passage 198. For example, as illustrated in the embodiment of FIG. 4, the valve body 240 may sealingly engage the valve seat 242 to substantially reduce or block fluid communication through the first passage 198.

According to various embodiments, the seal 220 may be moved as an entirety away from the valve seat 242 by the regulator spring 260. Accordingly, as illustrated in FIG. 3, the movement of the valve body 240 alone away from the valve seat 242 is merely exemplary. Further, the central portion 222 may be formed of a flexible material to allow movement of the valve body 240 relative to the valve seat 242 as discussed above.

As illustrated in FIGS. 3 and 4, the valve body 240 can move from an open position, as illustrated in FIG. 3, spaced away from the valve seat 242, to a closed position, as illustrated in FIG. 4, engaging the valve seat 242. The regulator spring 260 has a biasing force that may be selected to actuate the regulator valve 215 at a target pressure within the regulator chamber 210, which can also be maintained in the collection chamber 170 through the second passage 200. The biasing force of regulator spring 260 may be selected based upon various features and therapeutic requirements so that the regulator valve 215 is actuated at a target pressure. For example, the regulator spring 260 may be formed of a selected material, have a selected diameter, turn frequency, or the like to achieve closure of the regulator valve 215 at a target pressure within the regulator chamber 210. Further, some embodiments of the regulator 190 may include a pressure selector to adjust the regulation pressure. For example, the cap 194 and the base 196 may be threaded, and may be rotated to vary compression of the regulator spring 260, or a twist button or other member may engage the seal 220, including the valve body 240, to apply additional biasing force or to overcome a part of the biasing force of the regulator spring 260 to allow calibration of the regulated pressure in the regulator chamber 210. Accordingly, in some embodiments, the regulator 190 can regulate negative pressure to be about 75 mm Hg to about 200 mm Hg.

In operation, the regulator 190 may be normally open, as illustrated in FIG. 3, until the negative-pressure source 104 is connected and activated to distribute negative pressure through the first passage 198. After the negative-pressure source 104 has been activated, the absolute pressure within the regulator chamber 210 may be reduced as the seal between the protrusion 226 and the groove 228 is maintained and the central portion 222 of the seal 220 does not allow gases to pass from an exterior atmosphere into the regulator chamber 210. The regulator chamber 210 may become charged as the negative-pressure source 104 continues to draw gases through the first passage 198. Further, negative pressure can be distributed through the second passage 200 to the collection chamber 170 and to the dressing 102 if the regulator 190 is open.

If the target pressure is achieved in the regulator chamber 210, the biasing force of the regulator spring 260 may be overcome and the valve body 240 may move to the closed position and seal against the valve seat 242, as illustrated in FIG. 4.

Accordingly, the reduced pressure in the regulator chamber 210 caused by removal of air and gases from the regulator chamber 210 due to the negative-pressure source 104 can be maintained by the seal 220 until the biasing force of the regulator spring 260 is overcome and the valve body 240 engages the valve seat 242. The negative-pressure source 104 can provide unregulated negative pressure to the regulator chamber 210, and the regulator 190 can ensure that the negative pressure distributed to the collection chamber 170 does not exceed a target negative pressure.

The valve body 240 may be actuated by changes in negative pressure within the regulator chamber 210. For example, leaks in the system can cause the negative pressure within the collection chamber 170 to decrease over time. Because the collection chamber 170 is fluidly coupled to the regulator chamber 210, changes in the regulator chamber 210 may also be reflected in the collection chamber 170. The valve body 240 may open if the negative pressure in the collection chamber 170 decreases enough to allow the biasing force of the regulator spring 260 to move the valve body 240 from the valve seat 242.

Accordingly, the regulator 190, including the valve body 240, the valve seat 242, and the regulator spring 260, can maintain a target pressure within the collection chamber 170, and the dressing 102, that may be different from negative pressure provided by the negative-pressure source 104. In particular, if the negative-pressure source 104 is unregulated, the regulator 190 may provide a regulated pressure to the dressing 102, particularly if a negative pressure from the negative-pressure source 104 is greater than the target regulated pressure.

Figure 5:
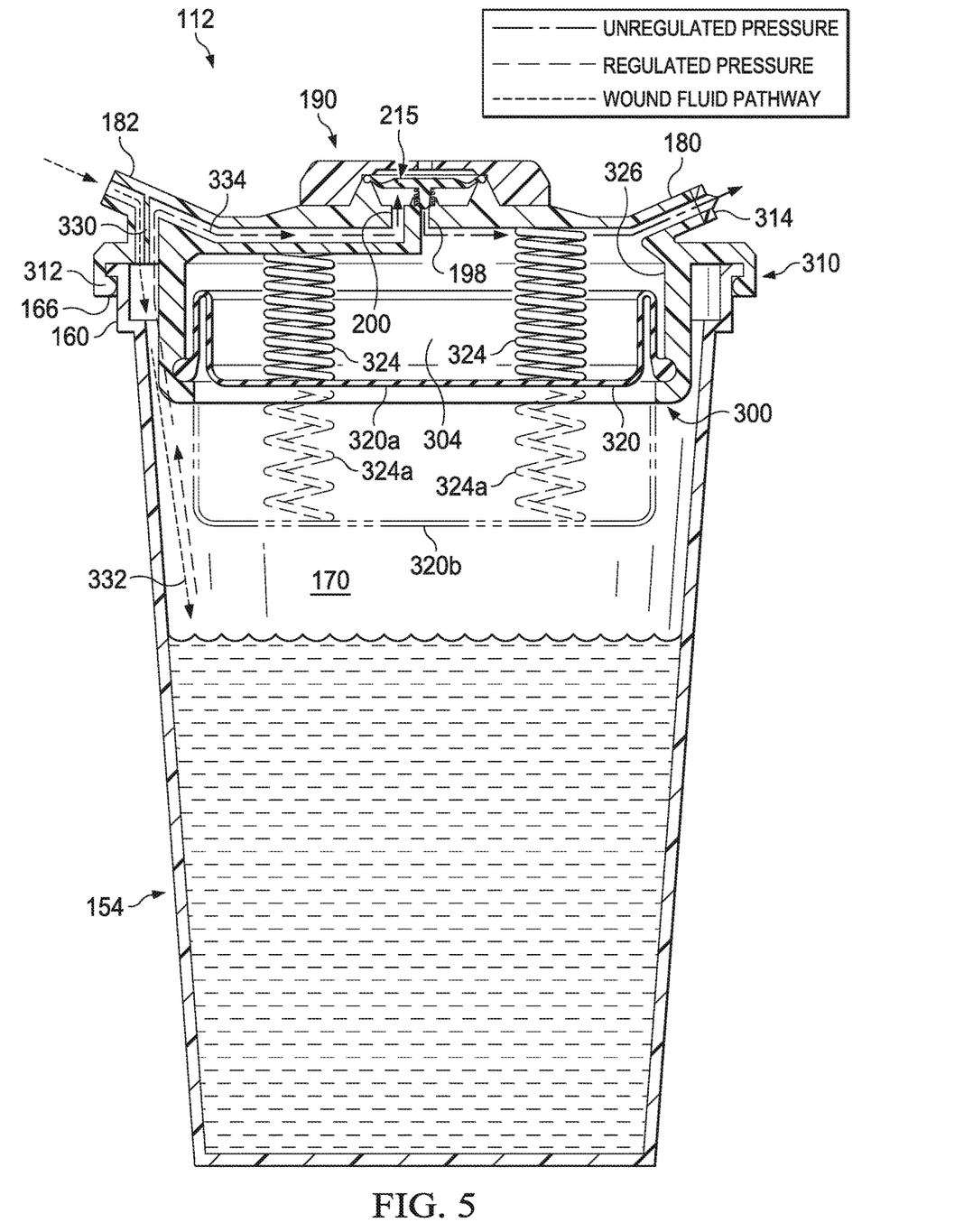
FIG. 5 is a cross-sectional view of a container of FIG. 1, according to various embodiments.

FIG. 5 illustrates details that may be associated with another example embodiment of the container 112. In the embodiment of FIG. 5, the container 112 may include the canister 154 and a lid 310. The lid 310 may be similar in many aspects to the canister lid 152. For example, the lid 310 may include the regulator 190, substantially as illustrated in FIG. 5. The lid 310 may also include a sealed connection to the canister 154, including a snap-fit or other appropriate fit at the rim 160 of the canister 154, including a lid connection portion (including a finger 312) and the canister connection portion 166. The connection of the lid 310 to the canister 154 can be substantially gas-tight to maintain a negative pressure.

The lid 310 may further include the downstream connector 180, which can be fluidly coupled to a primary negative-pressure source such as the negative-pressure source 104. A check valve 314 may be coupled to the downstream connector 180. Further, the lid 310 may include the upstream connector 182 that allows for a connection to the dressing 102.

The lid 310 may additionally comprise a secondary negative-pressure source, such as a reservoir 300. The reservoir 300 may include a piston, flexible wall, bellows, or membrane, such as a membrane 320, defining a negative-pressure chamber 304. The membrane 320 may be formed out of an appropriate material that is sufficiently flexible and substantially fluid impermeable, such as a medical grade silicone. The membrane 320 may further be formed to include a color that contrasts with the canister 154 or the lid 310 for viewing a position of the flexible membrane 320.

One or more springs 324 may bias the membrane 320 to a discharged position 320b. For example, in some embodiments, the springs 324 may be disposed in the negative-pressure chamber to expand the membrane to the discharged position 320b. Negative pressure in the reservoir 300 may overcome the biasing force of the springs 324 to allow the membrane 320 to contract to a charged position 320a.

The volume of the negative-pressure chamber 304 generally increases as the membrane 320 moves from the charged position 320a to the discharged position. The volume of the negative-pressure chamber 304 in the discharged state may vary to according to therapeutic requirements, but a volume in a range of about 100 milliliters to about 200 milliliters may be suitable for some applications. In some embodiments, the canister 154 may be transparent or may include a window through which the positon of the membrane 320 may be viewed to determine whether the reservoir 300 is charged. Graduation marks may provide additional indications of the state of the reservoir 300.

In some embodiments, the flexible membrane may be coupled to one or more supports 326 extending into the collection chamber 170. The membrane 320 may be sealingly engaged to the supports 326 to maintain a seal between the reservoir 300 and the ambient environment. In various embodiments, the membrane 320 may be welded, molded, or adhered to the supports 326. Further, a separate mechanical fixation member, such as a spring or locking member, may be used to engaged the flexible member against the supports 326. Thus, the reservoir 300 may maintain a negative-pressure charge relative to the atmosphere.

The negative-pressure source 104 can reduce the absolute pressure within the negative-pressure chamber 304 of the reservoir 300 formed by the flexible membrane 320 and the supports 326 of the lid 310. As the negative-pressure source 104 continues to reduce the absolute pressure within the negative-pressure chamber 304, the pressure within the negative-pressure chamber 304 is reduced relative to the collection chamber 170, and the flexible membrane 320 moves to compress the springs 324, as illustrated by the solid line indicating the flexible member charged position 320a and the solid compressed spring line 324. When compressed, the negative-pressure chamber 304 has a reduced absolute pressure relative to an atmospheric pressure. Accordingly, if the negative-pressure source 104 is disconnected from the downstream connector 180 or the container 112, such as for movement of the patient on which the dressing 102 is placed, the check valve 314 may fluidly seal the negative-pressure chamber 304, and the springs 324 can expand the flexible membrane 320 and increase the volume of the negative-pressure chamber 304 so that the auxiliary reservoir 300 can maintain a negative pressure relative to the dressing 102. The biasing by the springs 324 to the discharged position 320b can continue to generate negative-pressure in the negative-pressure chamber 304 through the second passage 200 relative to the upstream connector 182 through the regulator 190.

In an open state of the regulator 190, the first passage 198 may be fluidly coupled to the upstream connector 182 through the regulator chamber 210, the second passage 200, and the collection chamber 170. In a closed state of regulator 190, the second passage 200 and the collection chamber 170 may be fluidly isolated from the first passage 198. As illustrated in FIG. 5, the lid 310 may differ from the lid 152 by including a baffle 330 adapted to direct exudate away from the first passage 198 and into the collection chamber 170. In such an example configuration, exudate may move along fluid pathway 332 into the collection chamber 170, separating exudate from gas movement along a fluid pathway 334. Negative pressure from the reservoir 300 can maintain or ensure reduced pressure within the collection chamber 170 such that a negative pressure may be maintained in the dressing 102, at least temporarily, if the negative-pressure source 104 is disconnected from the container 112. Further, the regulator 190 can ensure that the pressure within the collection chamber 170 is regulated, regardless of whether the reduced pressure is directly from the negative-pressure source 104 or from the reservoir 300.

The systems, apparatuses, and methods described herein may provide significant advantages. For example, a regulator may be integrated into a fluid collection container, which can be used in a negative-pressure therapy system to regulate pressure applied to a tissue site. Such a regulator may be integrated or coupled to a lid adapted to fit generic canisters commonly available in health care environments, and may be particularly advantageous in facilities where unregulated wall suction is the primary source of negative pressure. The lid and regulator may be removable and re-usable, but it may be advantageous in some embodiments to weld or otherwise securely couple the lid to a canister. For example, securely coupling the lid to the canister can simplify proper disposal of exudate. Further, a container may additionally or alternatively include a secondary negative-pressure source, which can continue to provide therapeutic negative pressure to a tissue site if a primary negative-pressure source is disconnected or interrupted.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the negative-pressure source 104, or both may be eliminated or separated from other components for manufacture or sale. In other example configurations, the canister lid 152 and the regulator 190 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for providing negative-pressure therapy to a tissue site, the apparatus comprising:
   a container comprising a first fluid port, a second fluid port, and a collection chamber fluidly coupled to the second fluid port;
   a bellows disposed within the container, the bellows defining a negative-pressure chamber fluidly coupled to the first fluid port;
   a spring biasing the bellows to expand;
   a regulator having a regulator chamber that is integrated into the container;
   a first passage between the regulator chamber and the negative-pressure chamber;
   a second passage between the regulator chamber and the collection chamber; and
   a baffle disposed between the second fluid port and the second passage;
   wherein the regulator is configured to regulate negative pressure through the first passage.

2. The apparatus of claim 1, wherein the container comprises a canister and a lid, and the bellows is coupled to the lid.

3. The apparatus of claim 1, wherein the container comprises a canister and a lid, and the bellows and the regulator are integral to the lid.

4. The apparatus of claim 1, wherein the spring is disposed in the negative-pressure chamber.

5. The apparatus of claim 1, wherein:
   the regulator comprises a cap and a base coupled to the cap to define the regulator chamber; and
   the first passage is a first passage through the base and the second passage is a second passage through the base.

6. The apparatus of claim 1, wherein the regulator comprises a regulator valve configured to regulate negative pressure through the first passage based on changes to negative pressure in the regulator chamber.

7. The apparatus of claim 6, wherein the regulator valve is disposed in the regulator chamber.

8. The apparatus of claim 6, wherein the regulator valve is configured to close the first passage if negative pressure in the regulator chamber is greater than a target negative pressure, and to open the first passage if negative pressure in the regulator chamber is less than the target negative pressure.

9. The apparatus of any of claim 6, wherein the regulator valve comprises a regulator seal and a regulator spring operatively engaged with the regulator seal to bias the regulator valve away from the first passage.

10. The apparatus of claim 9, further comprising a valve seat adjacent to the first passage; wherein the regulator seal comprises a valve body adapted to sealingly engage the valve seat; and the regulator spring is operatively engaged with the valve body to bias the valve body away from the valve seat.

11. An apparatus for providing negative-pressure therapy to a tissue site, the apparatus comprising:
    a container comprising a canister, a lid, a first fluid port, a second fluid port, and a collection chamber fluidly coupled to the second fluid port;
    a bellows disposed within the container and coupled to the lid, the bellows defining a negative-pressure chamber fluidly coupled to the first fluid port;
    a spring biasing the bellows to expand;
    a regulator having a regulator chamber that is integrated into the container;
    a first passage between the regulator chamber and the negative-pressure chamber; and
    a second passage between the regulator chamber and the collection chamber;
    wherein the regulator is configured to regulate negative pressure through the first passage.

12. The apparatus of claim 11, further comprising a baffle disposed between the second fluid port and the second passage.

13. The apparatus of claim 11, wherein the bellows and the regulator are integral to the lid.

14. The apparatus of claim 11, wherein the spring is disposed in the negative-pressure chamber.

15. The apparatus of claim 11, wherein:
the regulator comprises a cap and a base coupled to the cap to define the regulator chamber; and
the first passage is a first passage through the base and the second passage is a second passage through the base.

16. The apparatus of claim 11, wherein the regulator comprises a regulator valve configured to regulate negative pressure through the first passage based on changes to negative pressure in the regulator chamber.

17. The apparatus of claim 16, wherein the regulator valve is disposed in the regulator chamber.

18. The apparatus of claim 16, wherein the regulator valve is configured to close the first passage if negative pressure in the regulator chamber is greater than a target negative pressure, and to open the first passage if negative pressure in the regulator chamber is less than the target negative pressure.

19. The apparatus of any of claim 16, wherein the regulator valve comprises a regulator seal and a regulator spring operatively engaged with the regulator seal to bias the regulator valve away from the first passage.

20. The apparatus of claim 19, further comprising a valve seat adjacent to the first passage; wherein the regulator seal comprises a valve body adapted to sealingly engage the valve seat; and the regulator spring is operatively engaged with the valve body to bias the valve body away from the valve seat.

21. An apparatus for providing negative-pressure therapy to a tissue site, the apparatus comprising:
a container comprising a canister, a lid, a first fluid port, a second fluid port, and a collection chamber fluidly coupled to the second fluid port;
a bellows disposed within the container, the bellows defining a negative-pressure chamber fluidly coupled to the first fluid port;
a spring biasing the bellows to expand;
a regulator having a regulator chamber that is integrated into the container;
a first passage between the regulator chamber and the negative-pressure chamber; and
a second passage between the regulator chamber and the collection chamber;
wherein the regulator is configured to regulate negative pressure through the first passage; and
wherein the bellows and the regulator are integral to the lid.

22. The apparatus of claim 21, further comprising a baffle disposed between the second fluid port and the second passage.

23. The apparatus of claim 21, wherein the spring is disposed in the negative-pressure chamber.

24. The apparatus of claim 21, wherein:
the regulator comprises a cap and a base coupled to the cap to define the regulator chamber; and
the first passage is a first passage through the base and the second passage is a second passage through the base.

25. The apparatus of claim 21, wherein the regulator comprises a regulator valve configured to regulate negative pressure through the first passage based on changes to negative pressure in the regulator chamber.

26. The apparatus of claim 25, wherein the regulator valve is disposed in the regulator chamber.

27. The apparatus of claim 25, wherein the regulator valve is configured to close the first passage if negative pressure in the regulator chamber is greater than a target negative pressure, and to open the first passage if negative pressure in the regulator chamber is less than the target negative pressure.

28. The apparatus of any of claim 25, wherein the regulator valve comprises a regulator seal and a regulator spring operatively engaged with the regulator seal to bias the regulator valve away from the first passage.

29. The apparatus of claim 28, further comprising a valve seat adjacent to the first passage; wherein the regulator seal comprises a valve body adapted to sealingly engage the valve seat; and the regulator spring is operatively engaged with the valve body to bias the valve body away from the valve seat.

* * * * *